US008738400B2

(12) United States Patent
Wedwick

(10) Patent No.: US 8,738,400 B2
(45) Date of Patent: May 27, 2014

(54) FRAME TRACER WEB BROWSER COMPONENT

(75) Inventor: David Wedwick, Phoenix, AZ (US)

(73) Assignee: Optivision, Inc., Phoenix, AZ (US)

( * ) Notice: Subject to any disclaimer, the term of this patent is extended or adjusted under 35 U.S.C. 154(b) by 0 days.

(21) Appl. No.: 13/493,668

(22) Filed: Jun. 11, 2012

(65) Prior Publication Data

US 2013/0144643 A1    Jun. 6, 2013

Related U.S. Application Data

(63) Continuation of application No. 12/069,677, filed on Feb. 12, 2008, now Pat. No. 8,200,502.

(60) Provisional application No. 60/889,898, filed on Feb. 14, 2007.

(51) Int. Cl.
    *G06Q 50/00*    (2012.01)
(52) U.S. Cl.
    USPC .............................................................. 705/2

(58) Field of Classification Search
    USPC ......................................................... 705/2, 26
    See application file for complete search history.

(56) References Cited

U.S. PATENT DOCUMENTS

2004/0215525 A1 *  10/2004  Keane et al. ..................... 705/26

* cited by examiner

*Primary Examiner* — John Pauls
(74) *Attorney, Agent, or Firm* — Allen J. Moss; Squire Sanders (US) LLP

(57) ABSTRACT

An internet browser software component facilitates online submission of prescription eyeglass orders by receiving frame trace data sent to a computer by a frame tracer and embedding it in an order form prepared for submission over the internet. The browser software component may interpret data sent to any peripheral port on the computer, including serial (COM) ports, Universal Serial Bus (USB) ports, and Ethernet ports. The browser software component embeds the frame trace so that it is sent in the same logical packet as the rest of the prescription order. The browser software component may also create a graphical representation of the frame trace and display it in a graphical user interface containing the order form so that the prescription order may be easily reviewed for accuracy before submitting it to be processed.

20 Claims, 3 Drawing Sheets

FIG. 1 - Prior Art vision)web
*Streamline. Simplify. Succeed.*

User Guide | Customer Service | Privacy Policy | Sign Out

| HOME | Order Now | Track Orders | Payer Transactions | My Account | CE/CME | News & Info | Technology Partners |

= Welcome Demo User =    Customer Service: 1-800-xxx-xxxx

[ New Order ]  [ Reuse Order ]  [ Redo Order ]    Create a new Rx lens order to send to a lab.

New Order [red asterisk denotes required field]    *Instructions*

Patient Last Name: Jones
Patient First Name: Tony

|    | Sphere* | Cylinder* | Axis* | Addition |
|----|---------|-----------|-------|----------|
| RE | -01.50  | -00.50    | 34    | +01.25   |
| LE | -01.75  | -00.75    | 55    | +01.25   |

( Show Prism )

| Dist. PD* | Dist. PD* | Near PD* | Dist. PD* | Height PD* | Height PD* |
|-----------|-----------|----------|-----------|------------|------------|
| 29.50     | 29.50     | 28.00    | 28.00     | 16.50      | 16.50      |
| (RE) mm   | (LE) mm   | (RE) mm  | (LE) mm   | (RE) mm    | (LE) mm    |

Laboratory*: VisionWeb Demo Lab - Austin, TX
This lab offers second pair orders
Billing/Shipping Account*: 123456/123456 vision)web

Job Type*: Remote Trace
Lens Type*: Bifocal

Lens Design*: Flat Top 28
Lens Material* Index:1.5: Polycarbonate

Available Treatments (Click Once To Add)
TD2
Reflection Free NP
Zeiss SET AR
Zeiss Gold ET
Zeiss Carat

Selected Treatments (Click Once To Remove)

TreatmentsComments to Lab (only for treatments)

Import Trace File
[ Browse ] ( Install Drivers )

| A Box* | B Box* | DBL* | ED |
|--------|--------|------|-----|
| mm     | mm     | mm   | mm  |

Frame Type: [Select]
Thickness Type: Lab decides best thickness
Thickness (RE) mm | Thickness (LE) mm

Frame Manufacturer | Style Name | Color | Temple Length mm

FRAME TRACER WEB BROWSER COMPONENT

CROSS-REFERENCE TO RELATED APPLICATIONS

This application is a continuation of and claims priority to U.S. application Ser. No. 12/069,677, filed Feb. 12, 2008 now U.S. Pat. No. 8,200,502 and entitled "Frame Tracer Web Browser Component" which claims priority to U.S. Provisional Appl. No. 60/889,898, filed Feb. 14, 2007 and entitled "Frame Tracer Browser Component," each of the foregoing applications being hereby incorporated by reference.

FIELD OF INVENTION

This invention relates to systems and methods for ordering prescription eyeglasses. This invention relates particularly to the software and method for ordering prescription eyeglasses over the internet by using an internet browser-based component to connect lab equipment such as a frame tracer to a web-based prescription lens order.

BACKGROUND

Frame tracers are computerized devices that measure the parameters of an eyeglass frame. Because each eyeglass frame can be unique in minute detail, the frame data measured from a frame tracer is critical to create exact results when manufacturing a pair of eyeglasses. A typical frame tracer will measure from 100 to as many as 1500 or more data points that describe the lens area of the frame, and many measure the right and left eyes independently. Additionally, the frame tracer measures other values including the curve of the frame and the distance between the right and left lenses. In this specification, the collection of measurements taken by a frame tracer of a single frame is referred to as a frame trace.

Conventionally, two separate sets of data are required to make prescription eyewear: the frame trace and the prescription. The prescription contains at least a patient's vision correction needs, and may also contain his name or other identifier, date of prescription, lens material or other information. As used herein, the prescription includes all data required to make prescription eyewear excluding the frame trace. In the conventional preparation of prescription eyewear, the eye care professional, such as an optometrist, ophthalmologist, optician, or an employee of one, generates the prescription order, which is then transmitted to the lens manufacturing laboratory. The eye care professional also sends the frame to the laboratory, either separately or with the prescription order. The laboratory associates the frame with the proper prescription order, measures the frame trace, and produce lenses to fit. The laboratory production process traditionally takes about seven days, mostly due to wait times for frame delivery and the order-association procedure.

More eyecare professionals are using frame tracers at their business locations instead of sending the frame to the lens manufacturer. It is therefore increasingly desirable to store the frame trace on an office computer in order to submit the data to a laboratory for creation of the lenses. However, the volume and type of data contained in one frame trace makes it prohibitive to manually process the data by retyping or reentering the data into a computerized order. To solve this problem, certain frame tracers can be connected to the office computer so that the frame trace can be transferred to the computer and stored on it. Unfortunately, however, due to format incompatibilities, this leaves the problem of storing the frame trace and prescription data in separate files. If transmitted to the lens maker, two files have to be transmitted or appended together, similar to the conventional order-association procedure. It would be desirable to integrate the frame trace with the prescription order.

The transmission of the frame trace to the office computer, however, does facilitate online ordering. An eye care professional enters the prescription order data into an internet-based form, associates the frame trace file to the form, and transmits the order either directly to the order recipient, namely the lens manufacturing laboratory's computer system or to a third party value-added service provider such as VisionWeb, www.visionweb.com, and Eyefinity, www.eyefinity.com. See FIG. 1 which shows a prior art example of importing a frame trace file so that the frame trace data are associated with the prescription order. Benefits to the eyecare professional include faster processing of the order because it is entered one time and the frame does not need to be delivered before processing and because error-checking and correcting are done at the time the order is entered. This can reduce the processing time to one or two days.

However, this system of online ordering is cumbersome: it requires a standalone program to receive the frame trace from the frame tracer, both the eyecare professional and the laboratory must manually match frame trace files to prescription orders, and an extensive file naming convention must be developed in order to maintain the proper association of frame traces to prescription orders. It would be advantageous to facilitate more direct communication between an internet browser and the frame tracer, so that frame trace information can be inserted directly into an online order.

Unfortunately, due to a design philosophy regarding security, an internet browser does not inherently access all resources of the office computer, such as devices that are peripherally connected to the computer via the computer's serial ports (COM ports). Frame tracers typically use the serial ports to connect to the host computer program. Because an internet browser does not access the serial ports directly, the internet browser cannot communicate with a frame tracer. It would be desirable to effectively connect the browser to the serial ports and thereby receive a frame trace.

Therefore, it is an object of this invention to provide a method for ordering prescription eyeglasses via the internet. It is a further object to provide an Internet browser software component that can communicate with a frame tracer connected to a computer and receive frame traces from the frame tracer. Another object of this invention is to provide an eyeglass ordering system that utilizes the internet browser software component.

SUMMARY OF THE INVENTION

The present invention increases the efficiency of the prescription eyeglass ordering process by allowing an eyecare professional to attach lab equipment such as a frame tracer to the eyecare professional's computer by any means, including a serial (COM port) cable, and to receive frame traces generated by the frame tracer directly into an order form for submission in an internet browser application. In this manner the parts of a prescription eyeglass order are seamlessly integrated and are transmitted to the order recipient simultaneously.

BRIEF DESCRIPTION OF THE DRAWINGS

FIG. 1 is a screen shot of the prior art showing attaching a frame trace to an online order.

DETAILED DESCRIPTION OF THE INVENTION

Figure 2:
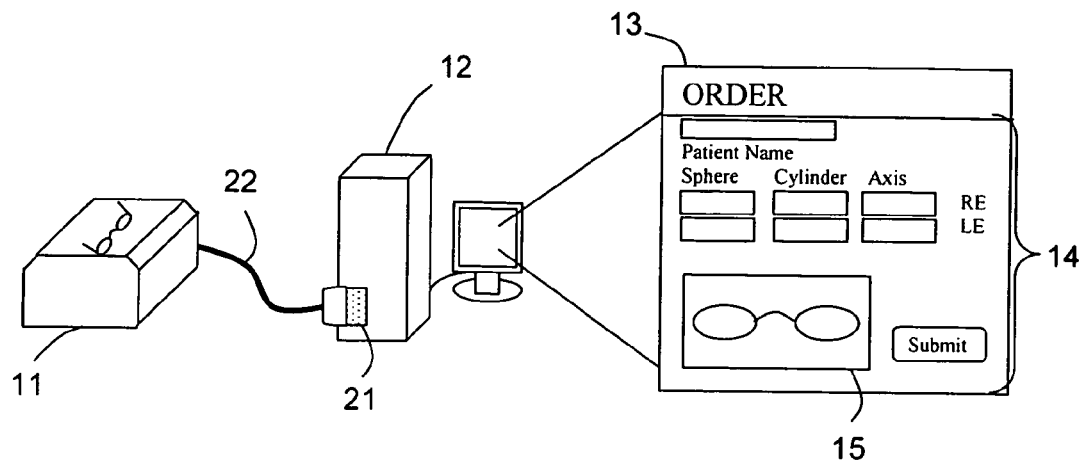
FIG. 2 illustrates an exemplary system for generating and processing a prescription eyeglass order as embodied in the invention.

Referring to FIG. 2, an exemplary eyeglass ordering system generates a complete prescription eyeglass order that can be sent to a lens manufacturing laboratory or a third party value-added service provider. The eyecare professional inserts a pair of eyeglass frames into the frame tracer 11 and activates it. The frame tracer 11 creates a frame trace and transmits it to the host computer 12 through the connection at serial port 21. The browser software component 20 receives the frame trace from the serial port 21, and translates it into perceivable data represented by the frame trace display 15. The browser software component 20 then embeds the frame trace display 15 in a graphical user interface ("GUI") 14, which is perceivable in the internet browser window 13. The eyecare professional then reviews the prescription eyeglass order displayed in the GUI 14 for accuracy and transmits the prescription eyeglass order via internet to a lens manufacturing laboratory or a third party value-added service provider.

The eyeglass ordering system may have components that are located proximate to or remote from each other. In the preferred embodiment, the components of the eyeglass ordering system are located in the office of an eyecare professional, allowing the eyecare professional to exert full control over generation of the order. A frame tracer 11 connects to a host computer 12 at an available peripheral port such as a serial port 21. The frame tracer 11 can be any commercially available frame tracer, such as the LT-900 Remote Tracer by Santinelli® or the Optronics® 4T Frame Tracer. The host computer 12 can be any personal computer or other computing system which comprises components capable of establishing an internet connection, implementing an internet browser program, and connecting to the frame tracer 11. In the preferred embodiment, the host computer 12 is a personal computing system that includes a monitor, an internet connection, and at least one serial port.

The connection between the frame tracer 11 and the host computer 12 can be made by any means for connecting peripheral components to a personal computer, including Universal Serial Bus (USB), serial (COM port) connections, ethernet or other network connections, or intermediate connectors such as a wired or wireless TWAIN server. In the preferred embodiment, the host computer 12 includes a serial port 21 and the frame tracer 11 connects to the serial port 21 with a serial cable 22. This connection allows the frame tracer 11 to transmit frame traces to the host computer 12 for processing.

Figure 3:
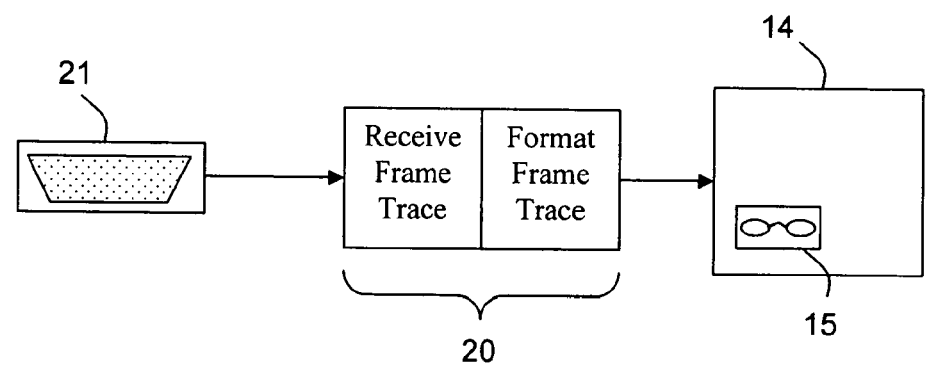
FIG. 3 is a schematic view of a browser software component for receiving, translating, and embedding frame traces.
Figure 4:
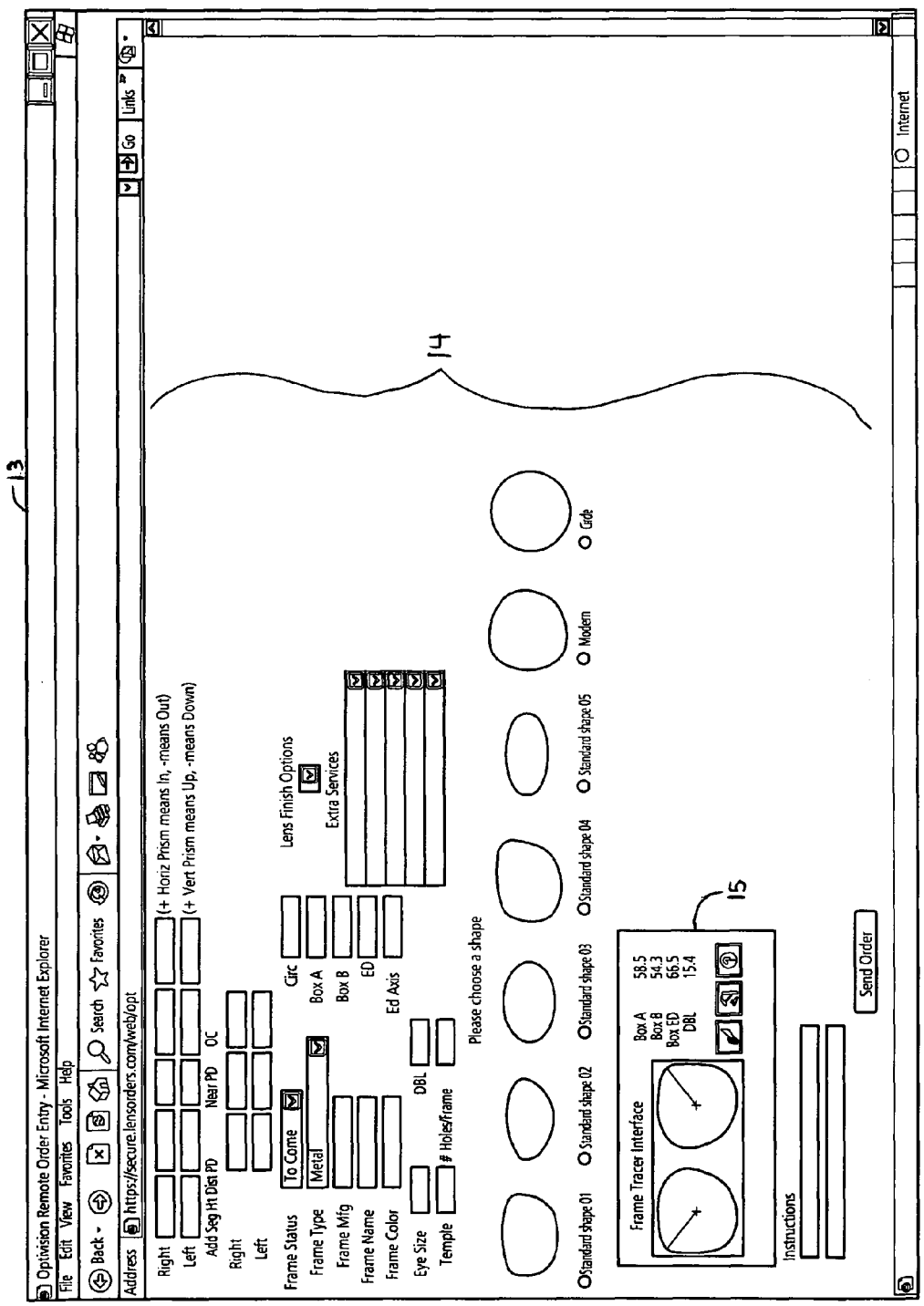
FIG. 4 is an online order form of the present invention incorporating prescription data and frame trace data.

Referring to FIG. 3, the browser software component 20 comprises computer program code devices that allow the browser software component 20 to communicate with the frame tracer 11 and transfer data to the internet browser and subsequently to the GUI 14. In the preferred embodiment, the browser software component 20 accesses a frame trace that has been provided by the frame tracer 11 to the serial port 21, translates the information into a format that can be perceived when displayed in the GUI 14, and transmits the frame trace to the GUI 14 displayed within the internet browser window 13. The GUI 14 then generates the frame trace display 15. As seen in FIGS. 2 and 4, the frame trace display 15 is a graphical representation of the shape of the frame. Preferably the data from the frame tracer or other lab equipment is normalized so that the data from all lab equipment are produced in the same format. The frame trace is thereby incorporated into the eyeglass prescription order and can be reviewed by the eyecare professional before order submission.

The browser software component 20 transfers the frame trace to the GUI 14 displayed within the internet browser window 13 using a communication method that allows browser-hosted plug-ins or components to communicate with the web browser, such as Java, JavaScript, LiveConnect, or any similar communication method. In the preferred embodiment, the browser software component 20 utilizes LiveConnect to transfer the frame trace. The GUI 14 contains a form which is implemented using an internet application programming language such as hypertext markup language (HTML), hypertext preprocessor (PHP), Java, JavaScript, or Perl. When the frame trace arrives at the GUI 14 the browser software component 20 embeds it in the form and creates a frame trace display 15 that can be perceived by the eyecare professional. The browser software component 20 is designed to overcome the limitations of internet browsers and other browser software components that cannot communicate with peripheral connections. The browser software component 20 can be created using any now known or later developed software component design technology that can communicate with peripheral connections, including Microsoft® ActiveX® or other Component Object Model designers, Microsoft® .NET®, Apple® Dashboard®, and NPAPI (Netscape® Plug-in Application Programming Interface). In the preferred embodiment, the browser software component 20 is an ActiveX control. The browser software component 20 embeds the frame trace data in the GUI 14, so that the frame trace data is enclosed within the same data packet as the rest of the prescription order data when the order is submitted.

The host computer 12 contains software necessary to display an internet browser window 13 at a user's request. The internet browser called by the user may be any computer program capable of interpreting one or more file transfer protocols now known, such as HTTP, HTTPS, or FTP, or later developed; for example, the internet browser may be Microsoft Internet Explorer, Mozilla Firefox, Netscape, Apple's Safari, or Opera. In the preferred embodiment, the internet browser window 13 is generated by Microsoft Internet Explorer. Referring to FIG. 4, the internet browser window 13 displays the GUI 14 which includes a form into which the eyecare professional enters data for a prescription order. Additionally, the GUI 14 includes the frame trace display 15, created by the browser software component 20 using the frame trace provided by the frame tracer 11. When all data has been entered and the frame trace is successfully transmitted to the GUI 14, the eyeglass order can be reviewed prior to submission. The order, comprising the entered data and the frame trace, is then sent as a single logical packet via the internet to a lens manufacturing laboratory or a third party value-added service provider.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

The invention claimed is:

1. A non-transitory computer-readable medium comprising computer program product for processing prescription eyeglass order data, the product comprising computer readable program code for:
   receiving a frame trace from a frame tracer that is operably connected to a host computer; and
   embedding the frame trace into a prescription order displayed using an internet browser, wherein embedding the frame trace does not comprise appending a frame trace data file; and wherein the frame trace comprises a graphical representation of the shape of a pair of eyeglass frames.

2. The computer program product of claim 1, wherein the prescription order is sent to an order recipient via the internet.

3. The computer program product of claim 1, further comprising computer readable program code for:
   formatting the frame trace for human-readable display.

4. The computer program product of claim 3, wherein the frame trace is displayed in the internet browser window simultaneously with the prescription order into which the frame trace is embedded.

5. The computer program product of claim 1, wherein the frame tracer is connected to the host computer at a peripheral port.

6. The computer program product of claim 5, wherein the peripheral port is a serial port.

7. The computer program product of claim 5, wherein the peripheral port is a Universal Serial Bus (USB) port.

8. The computer program product of claim 5, wherein the peripheral port is an Ethernet port.

9. The computer program product of claim 1, wherein the prescription order is submitted to a lens manufacturing laboratory through the internet.

10. The computer program product of claim 9, wherein the prescription order is submitted as a single logical packet.

11. A non-transitory computer-readable medium comprising computer program product for processing prescription eyeglass order data, the product comprising computer readable program code for:
    receiving a frame trace from a frame tracer connected to a host computer;
    creating a graphical representation of the frame trace;
    embedding the frame trace into a prescription order formatted for submission using an internet browser, wherein embedding the frame trace does not comprise appending a frame trace data file; and wherein the frame trace comprises a graphical representation of the shape of a pair of eyeglass frames; and
    displaying the graphical representation of the frame trace in an internet browser window simultaneously with the prescription order into which the frame trace is embedded.

12. A non-transitory computer-readable medium comprising computer program product for processing prescription eyeglass order data, the product comprising computer readable program code for:
    upon activation of a frame tracer by an operator of the frame tracer, receiving at a browser software component a frame trace of a pair of eyeglasses frames from the frame tracer;
    translating, by the browser software component, the frame trace into perceivable data represented by a frame trace display, wherein the translating comprises formatting the frame trace for human-readable display, wherein the frame trace display, as formatted, provides a graphical representation of the shape of the pair of eyeglasses frames;
    embedding the frame trace display in a graphical user interface, which is perceivable in an internet browser window, wherein the graphical user interface comprises a form, wherein the embedding comprises embedding textual and graphical data to be displayed; and
    displaying the frame trace display including the textual and graphical data on the monitor in the internet browser window, by the graphical user interface, wherein the graphical user interface also simultaneously displays a prescription order contained in the same internet browser window, wherein displaying the frame trace comprises displaying textual and graphical data regarding the frame trace.

13. A method performed on a machine for processing prescription eyeglass order data, the method comprising:
    receiving a frame trace from a frame tracer that is operably connected to a host computer; and
    embedding the frame trace into a prescription order display using an internet browser, wherein embedding the frame trace does not comprise appending a frame trace data file; and wherein the frame trace comprises a graphical representation of the shape of a pair of eyeglass frames.

14. The method claim 13 wherein the prescription order is sent to an order recipient via the internet.

15. The method of claim 13 further comprising:
    formatting the frame trace for human-readable display; and
    displaying the frame trace in an internet browser window.

16. The method of claim 15 further comprising:
    displaying the frame trace in the internet browser window simultaneously with the prescription order into which the frame trace is embedded.

17. The method of claim 13, further comprising:
    submitting the prescription order to a lens manufacturing laboratory through the internet.

18. The method of claim 17, further comprising:
    submitting the prescription order as a single logical packet.

19. The method of claim 13, wherein the receiving the frame trace comprises receiving the frame trace on a peripheral port.

20. The method of claim 19, wherein the peripheral port is a Universal Serial Bus (USB) port.

* * * * *